(12) United States Patent
Ebara et al.

(10) Patent No.: US 6,281,972 B1
(45) Date of Patent: Aug. 28, 2001

(54) METHOD AND APPARATUS FOR MEASURING PARTICLE-SIZE DISTRIBUTION

(75) Inventors: Kensei Ebara; Shoichiro Shin, both of Tsukuba (JP)

(73) Assignee: Japan as represented by Director General of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/508,666

(22) PCT Filed: Mar. 31, 1999

(86) PCT No.: PCT/JP99/01691
§ 371 Date: Mar. 22, 2000
§ 102(e) Date: Mar. 22, 2000

(87) PCT Pub. No.: WO00/08437
PCT Pub. Date: Feb. 17, 2000

(30) Foreign Application Priority Data
Aug. 4, 1998 (JP) .................................. 10-220029

(51) Int. Cl.[7] .................................. G01N 15/02
(52) U.S. Cl. .................. 356/336; 356/335; 356/337; 356/338
(58) Field of Search ................... 356/335, 336, 356/337, 338, 339, 340, 341, 342, 343, 72, 73

(56) References Cited

U.S. PATENT DOCUMENTS 4,633,714 * 1/1987 Mazumder et al. .................. 356/336
5,296,910 * 3/1994 Cole ...................................... 356/336

* cited by examiner

Primary Examiner—Frank G. Font
Assistant Examiner—Roy M. Punnoose
(74) Attorney, Agent, or Firm—Oblon, Spivak, McClelland, Maier & Neustadt, P.C.

(57) ABSTRACT

An apparatus for measuring particle size distribution comprises an electric mobility classifying section (11) that comprises an outside electrode (12), an inside electrode (13) and an annular cylindrical hollow portion (14) defined by the outside and inside electrodes, a particle size measuring section (21) that is disposed under the electric mobility classifying section for measuring particle size distribution, and a guide frame (31) that allows the electric mobility classifying section and the annular cylindrical hollow section to communicate with each other. A sample gas containing charged particles under measurement is supplied from above into the annular cylindrical hollow section of the electric mobility classifying section to classify the particles according to their electric mobilities. The gas containing the classified particles is supplied into the particle size measuring section via the guide frame to directly obtain approximate particle sizes. The number of charges of the particles is obtained from the electric mobility and the approximate particle sizes. Precise particle sizes are determined from the number of charges and the electric mobilities.

2 Claims, 2 Drawing Sheets

METHOD AND APPARATUS FOR MEASURING PARTICLE-SIZE DISTRIBUTION

FIELD OF ART

The present invention relates to a method and apparatus for measuring particle size distribution of particles suspended in a gas with great ease and high precision.

BACKGROUND ART

As an apparatus for classifying particles suspended in a gas by their electric mobilities, one is disclosed in the Journal of Aerosol Science, Vol. 16, pp. 443–452, "Aerosol Classification by Electric Mobility" by E. O. Knutson and K. T. Whitby (Reference 1).

The prior art classifying apparatus per se can only classify particles by their electric mobilities. However, by connecting the condensation nucleus type counter device disclosed in "Aerosol Technology" (Wiley Interscience 1982), p. 262 by W. C. Hinds (Reference 2) to the aforementioned apparatus for classifying particles by their electric mobilities and counting the number of the classified particles at various electric mobility values, it is possible to measure electric mobility distribution with high precision.

In the Journal of Aerosol Science Vol. 9, pp. 41–54 (1978), "Determination of the Aerosol Size Distribution from the Mobility Distribution of the Charged Fraction of Aerosol" by W. A. Hoppel (Reference 3), there is described a data processing method for converting the electric mobility distribution obtained as described above into particle size distribution.

However, the data processing method relates to a method for solving a problem falling in the category of so-called inverse problems. Owing to the nature of such problems, there are cases where no solution exists and where the uniqueness or stability of a solution is not assured. For these reasons, there are some cases that fail to measure particle size distribution or give rise to a large error in the particle size distribution measured.

Examples of methods for directly measuring particle size distribution of particles suspended in a gas include the light-scattering method using a light-scattering type automatic particle counter prescribed by JIS-B-9921 (Reference 4), the method using an impactor, described in "Applied Aerosol Technology" (Yokendo, 1984), p. 262 by Mikiji Takahashi (Reference 5) and the aerosol beam method described in "Applied Aerosol Technology" (Yokendo 1984) p. 264 by Mikiji Takahashi (Reference 6).

However, these methods for the direct measurement of particle size distribution have difficulty in measuring a particle size distribution with high precision.

In view of the above, an object of the present invention is to provide a measuring method and a measuring apparatus that can measure particle size distribution of particles suspended in a gas with precision higher than that obtained in the conventional methods of measuring particle size distribution by obtaining particle sizes from the electric mobility and number of charges of individual particles without using any analytical means.

DISCLOSURE OF THE INVENTION

In order to attain the object described above, the method for measuring particle size distribution according to the present invention is characterized by classifying particles suspended in a gas according to their electric mobilities, then using a particle size measuring method to directly obtain approximate values of particle sizes, obtaining the number of charges on the particles from the electric mobilities and the approximate particle sizes thus obtained, and determining the precise particle sizes from the number of charges thus obtained and the electric mobilities.

An apparatus for measuring particle size distribution according to the present invention is characterized by comprising an electric mobility classifying section that comprises an outside electrode, an inside electrode and an annular cylindrical hollow portion defined by the outside and inside electrodes, a particle size measuring section disposed under the electric mobility classifying section for measuring approximate particle sizes, and a guide frame that allows the electric mobility classifying section and the annular cylindrical hollow section to communicate with each other; supplying from above a sample gas containing charged particles under measurement into the cylindrical hollow section of the electric mobility classifying section to classify the particles according to their electric mobilities; supplying the gas containing the classified particles into the the particle size measuring section via the guide frame to directly obtain approximate particle sizes; obtaining the number of charges of the particles from the approximate particle sizes; and determining precise particle sizes from the number of charges and the electric mobilities.

Since the present invention determines particle sizes from the electric mobilities according to which particles are classified and the number of charges, as described above, it enables measurement of particle size distribution with high precision.

BEST MODE FOR WORKING THE INVENTION

The present invention will be described in detail with reference to the accompanying drawings.

Figure 1:
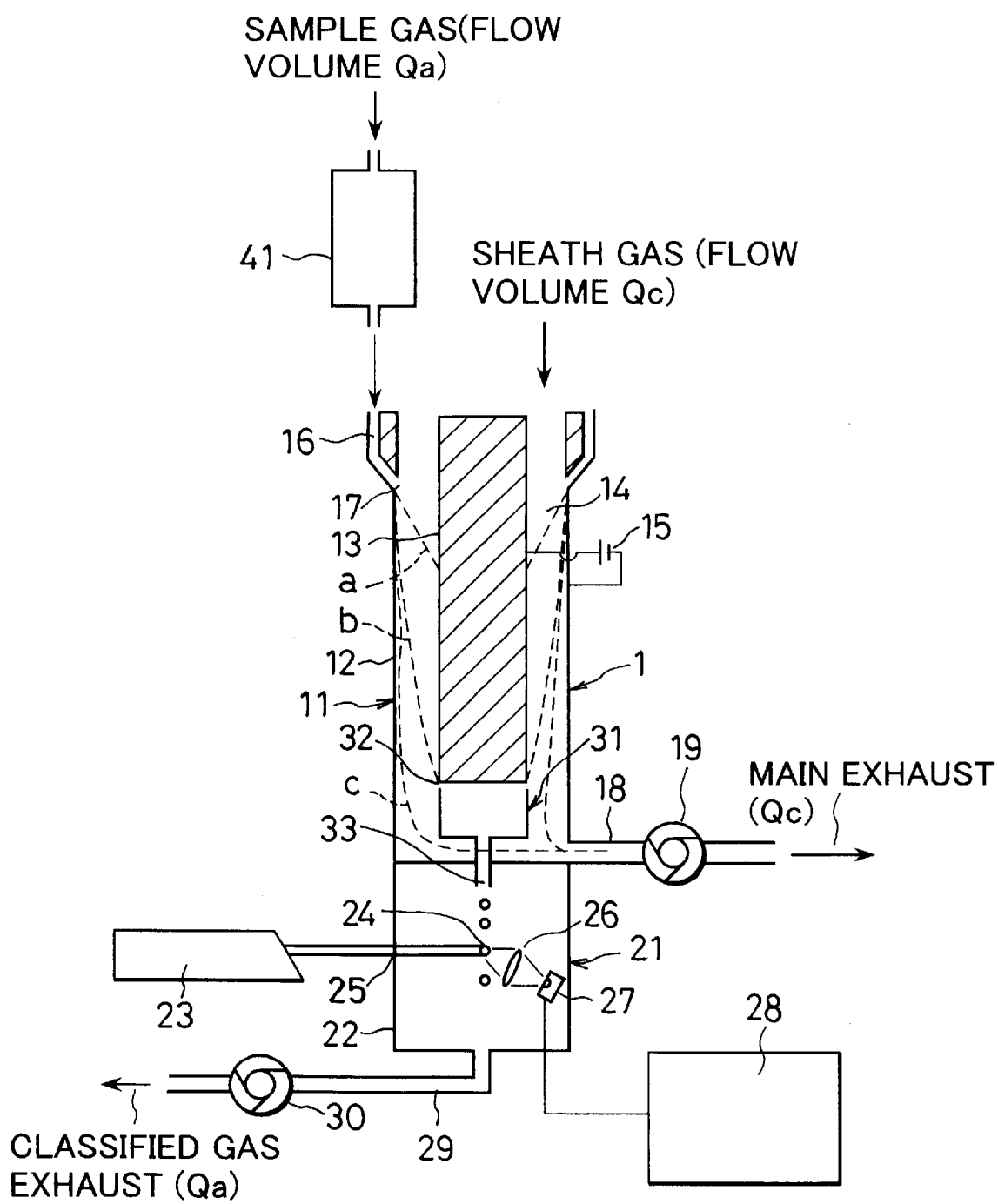
FIG. 1 is a schematic view showing one embodiment of the particle size distribution measuring apparatus according to the present invention, and FIG. 2 an explanatory view illustrating the principle of obtaining particle size distribution, in which (a) is a schematic view showing one example of unknown particle size distribution under measurement, (b) a diagram showing the sum of an electric mobility distribution corresponding to the particle size distribution of (a) and distributions corresponding to the numbers of charges, (c) a diagram showing the particle size distribution of the particles classified in the electric mobility classifying section, and (d) a schematic view showing particle size distribution spectra obtained by measuring the particle size distribution of (c) by estimate in the particle size measuring section.

FIG. 1 schematically illustrates the configuration of an apparatus 1 for measuring the particle size distribution of particles suspended in a gas according to the present invention.

The particle size distribution measuring apparatus 1 comprises an electric mobility classifying section 11 and a particle size measuring section 21 which are disposed vertically, and a guide frame 31 which allows the electric mobility classifying section 11 and the particle size measuring section 21 to communicate with each other.

The electric mobility classifying section 11 comprises a cylindrical outside electrode 12 and a columnar inside electrode 13 concentrically disposed in the outside electrode 12 to define a ring-like cylindrical hollow portion 14 therebetween. A variable DC power supply 15 is connected to the two electrodes to apply voltage thereto.

The outside electrode 12 is provided its upper peripheral edge with a ring-like inlet frame 16 into which a sample gas is supplied. The lower end of the inlet frame 16 is formed with an inlet slit 17 open to the upper end of the cylindrical hollow portion 14.

The cylindrical hollow portion 14 has a bottom that partitions it from the particle size measuring section 21. A first exhaust passage 18 is connected to the lower end surface of the cylindrical hollow portion. A first exhaust pump 19 is provided midway the first exhaust passage 18.

The guide frame 31 is positioned below the inside electrode 13. Between the lower end of the inside electrode 13 and the upper end of the guide frame 31 is formed an outlet slit 32.

The gas flowing downward inside the cylindrical hollow portion 14 enters the guide frame 31 via the outlet slit 32 and flows into the particle size measuring section 21 via a diameter-reduced nozzle 33 provided on the lower end of the guide frame.

The particle size measuring section 21 shown in FIG. 1 may have any configuration insofar as the particle size distribution of particles contained in a gas can be measured by the light-scattering method, method using an impactor, aerosol beam method, etc. The particle size measuring apparatus shown in FIG. 1 uses the light-scattering method.

The particle size measuring section 21 comprises a closed housing frame body 22. Outside the housing frame body there is provided a light source 23. Inside the housing frame body a light-irradiated portion 24 is set in place beneath the nozzle 33 and irradiated with light transmitted from the light source 23 and passing through a light transmitting portion 25 of the housing frame body 22, that is a glass window or the like. The light scattered by the particles passing through the light-irradiated portion 24 is focused by a lens 26 on a photo-electric converter 27 where the scattered light is converted into pulse voltage. A pulse height value determined according to the particle size is produced by a pulse height analyzer 28 connected electrically to the photo-electric converter 27.

An exhaust passage 29 for classified gas is connected to the bottom of the housing frame body 22, and a second exhaust pump 30 is provided midway the exhaust passage 29.

A charging unit 41 is provided above the inlet frame 16 for charging the particles contained in a gas to be supplied into the inlet frame.

The particle size distribution measuring apparatus 1 of the present invention is configured as described above. A method for measuring the particle size of particles suspended in a gas using the particle size distribution measuring apparatus 1 will now be described hereinafter.

A sample gas containing particles under measurement is passed through the charging unit 41 to charge the particles. The second exhaust pump 30 is driven to bring the interior of the electric mobility classifying section 11 and that of the particle size measuring section 21 to a negative pressure state, thereby inducing a sucking action. The sample gas containing the charged particles is supplied from the inlet frame 16 and passed successively through the electric mobility classifying section 11 and through the particle size measuring section 21.

In the electric mobility classifying section 11, only particles having electric mobility in a specific narrow range are selected from the particles contained in the sample gas.

The principle will be described in detail. By passing the sample gas through the charging unit 41, e.g. one utilizing a radiation source such as americium 241 etc., some of the particles are charged. At that time, probability f(p;D) of particles having a particle size of D being charged with charges whose number of charges is p (provided that p=0, ±1, ±2, . . . ) is determined by the characteristics of the charging unit 41. For example, it is known that the charging unit utilizing a radiation source approximates to the Boltzmann distribution.

The sample gas passed through the charging unit 41 passes through the inlet slit 17 from the inlet frame 16 and is introduced in a flow volume of Qa into the cylindrical hollow portion 14. In addition to the sample gas, a sheath gas stationarily flows into the cylindrical hollow portion 14 from the top opening thereof in a flow volume of Qc owing to the suction force produced by the driven first waste pump 19, while keeping a laminar flow state.

Therefore, the sample gas containing the charged particles and the sheath gas flow in the cylindrical hollow portion 14 in the total flow volume of (Qa+Qc).

A constant voltage V is applied by the variable DC power supply 15 to the outside electrode 12 and the inside electrode 12 to produce an electrostatic field. The charged particles having a large electric mobility move along a trajectory a shown in FIG. 1 toward the inside electrode 13 under the influence of the electrostatic field. The charged particles having a small electric mobility move along a trajectory c shown in FIG. 1 and are discharged by an amount corresponding to the flow volume Qc together with the gas from the first exhaust passage 18 by the driven first exhaust pump 19.

The classified particles having electric mobility in the specific narrow range flow into the guide frame 31 from the outlet slit 32 in an amount corresponding to the flow volume Qa together with the gas, whereafter they are supplied from the nozzle 33 into the particle size measuring section 21.

Since the range of the electric mobility of the particles thus classified in the electric mobility classifying section 11 and supplied into the particle size measuring section 21 is directly proportional to the flow volume ratio Qa/Qc, adoption of a small flow volume ratio enables the electric mobility value of the classified particles to be obtained with high precision. In addition, the center value of the electric mobility can be optionally adjusted by changing the voltage V.

The particles thus classified on the basis of the electric mobility in the very narrow range are, as described above, introduced into the particle size measuring section 21 where the particle size distribution of the particles is to be measured.

The principle of the light-scattering method that directly measures the particle size distribution of particles will be described with reference to FIG. 1. Particles contained in a gas pass through the light-irradiated portion 24 formed by the light source 23 and scatter the light. The volume of the light-irradiated portion 24 is sufficiently throttled so as not to generate a phenomenon that the particles pass through two or more light-irradiated portions 24 more often than not.

The light scattered by the particles at the light-irradiated portion 24 is focused by the lens 26 and then converted by the photoelectric converter 27 into pulsed voltage. Since the pulse height of the voltage is determined by the particle size, the particle size distribution can be measured by using the pulse height analyzer 28 to obtain the number of pulses at each pulse height. According to the light-scattering method, however, the scattered light intensity varies, even when particles have the same size, depending upon the spatial and temporal fluctuation of the irradiated light intensity at the irradiated portion 24, optical reflectance of the particles, spatial posture of nonspherical particles, etc. For this reason, the particle size measured by this method is not precise but merely estimative.

The gas containing the particles within the particle size measuring section 21 is discharged at the flow volume Qa by the driven second exhaust pump 30.

The principle of measuring particle size distribution with precision from the estimated value obtained at the particle size measuring section 21 will be descried in detail with reference to FIG. 2.

Figure 2A:
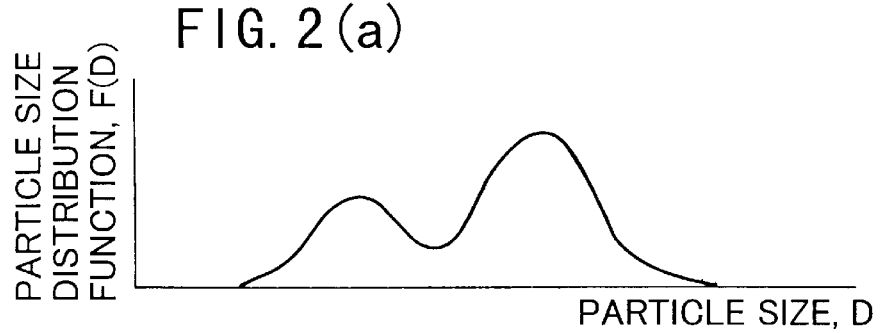

An unknown particle size distribution F(D) of the particles contained in the sample gas is schematically shown in FIG. 2(a). The particles are given the number p of charges in accordance with the probability f(p;D) determined as described above by the characteristics of the charging unit 41.

The electric mobility Z of particles having a particle size D and the number p of charges is expressed by:

$$Z = peC(D)/3\pi\eta D \qquad (1)$$

wherein $\pi$ denotes the ratio of the circumference of a circle to its diameter, e the quantum of electricity, p the number of charges, C(D) the Cunningham correction factor, and $\eta$ the coefficient of viscosity.

Therefore, the electric mobility of the particles has a distribution G(Z) determined by F(D), f(p;D) and relational expression (1).

Figure 2B:
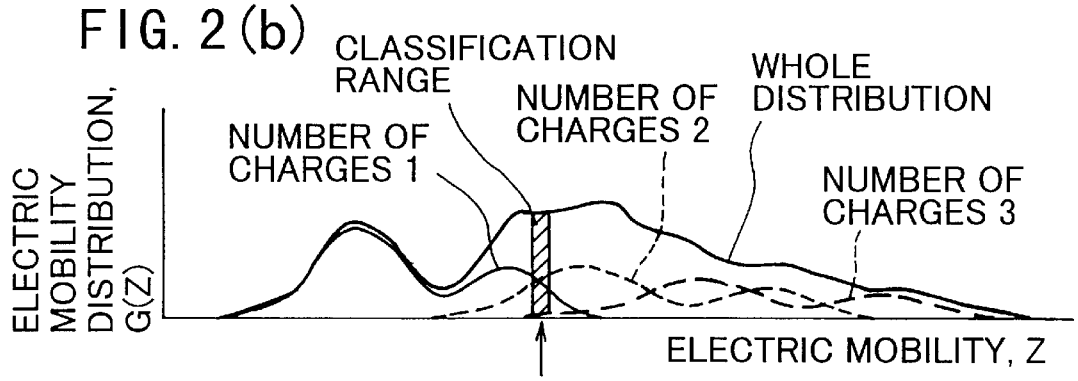

As shown schematically in FIG. 2(b), the distribution G(Z) is a combination of the electric mobility distribution (shown by the thin solid line) of the particles whose number of charges p is 1, that (shown by the dotted line) of the particles whose number of charges p is 2, that (shown by the dashed line) of the particles whose number of charges p is 3, etc.

As schematically shown by the oblique line-shaded part in FIG. 2(b), particles having a specific small range of electric mobilities are selected at the electric mobility classifying section 11 from the particle-containing sample gas that has passed through the charging unit 41 and entered the electric mobility classifying section 11 via the inlet frame 16.

Since the electric mobility of the selected particles is determined by the voltage V applied between the outside electrode 12 and the inside electrode 13, it is hereinafter referred to as Z(V).

Figure 2C:
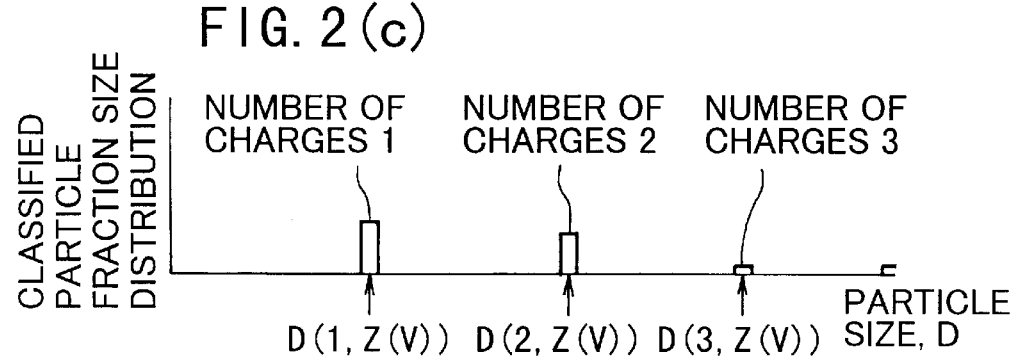

The classified particles having the electric mobility of Z(V) comprise particles having different numbers of charges, and their particle sizes differ depending on the number p of charges and have distributions as shown in FIG. 2(c). That is to say, due to the fact that the classification range of the electric mobility is narrow as shown in FIG. 2(b), when the number of charges is determined, the corresponding particle size range is also narrow. For this reason, the particle size distribution has separately arranged parts of narrow distribution widths as shown in FIG. 2(c).

Figure 2D:
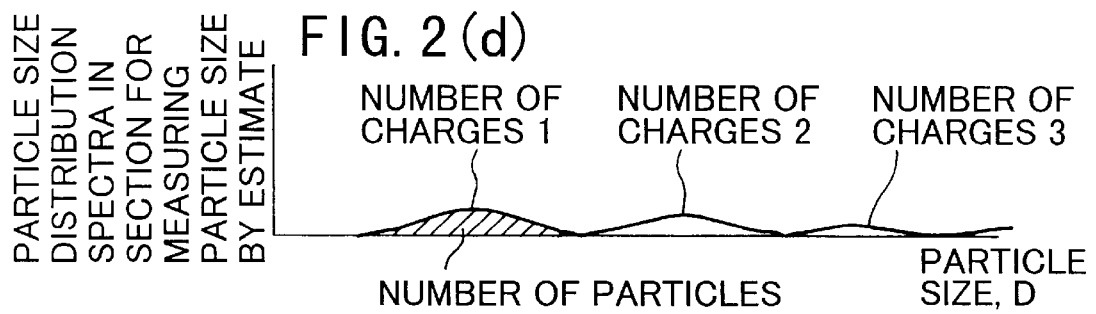

By measuring the particle size distribution of these particles at the particle size measuring section 21, a particle size distribution spectrum divided into some partial spectra can be obtained as shown in FIG. 2(d).

The widths of the partial spectra shown in FIG. 2(d) are larger and the heights thereof are shorter than those of the distributions shown in FIG. 2(c). This indicates that the measurement precision at the particle size measuring section 21 is not high.

At this time, the numbers p of charges corresponding respectively to the partial spectra are unknown. However, the number p of charges corresponding to each partial spectrum can be determined by using Z(V) and calculating particle sizes D(p;Z(V)) corresponding respectively to p=1, 2, 3, . . . in accordance with expression (1) and conducting a search as to what partial spectrum containing D(p;Z(V)) corresponds to what number p of charges. Since the number p of charges is a dispersed value in that instance, the number p of charges obtained is strict and includes no error insofar as the precision of measurement at the particle size measuring section 21 is secured to such an extent that the partial spectra shown in FIG. 2(d) do not overlap.

A partial spectrum having a specific number of charges (p=1, for example) will now be discussed. When the number of particles is obtained (calculated from the area of the leftmost mountain-shaped partial spectrum shown in FIG. 2(d), that is the shaded portion under the spectral curve), it conforms to the number of particles having a particle size D=D(p;Z(V)) of the particles in the sample gas and conforming to the value of the cited number p of charges. Therefore, when the number of such particles is obtained while successively varying the voltage V applied to the two electrodes 12 and 13, it is possible to obtain the particle size distribution Fp(D) of the particles having the cited number p of charges, that is part of the original particle size distribution F(D).

As described in the foregoing, since the ratio f(p;D) of the number of particles having the particle size D and the number p of charges relative to the total number of particles is known in advance as a characteristic of the charging unit 41, it is possible to obtain the particle size distribution aimed at, using the f(p;D) and the thus obtained Fp(D), from relational expression:

$$F(D) = Fp(D)/f(p;D) \qquad (2)$$

Since in the method described above the function of the particle size measuring section 21 is to measure the number of charges corresponding to each partial spectrum, the measurement precision of F(D) will not deteriorate insofar as the partial spectra shown in FIG. 2 do not overlap, notwithstanding that the particle size measurement precision at the estimative particle size measuring section is low. Since the particle size distribution therefore does not rely on the particle size measurement precision at the particle size measuring section 21 if the flow volume Qa/Qc at the electric mobility classifying section 11 is set at a sufficiently small value, it is possible to measure the particle size distribution with high precision. Moreover, since this method does not require inverse problems to be solved, a particle size distribution can be obtained irrespective of the kind of particle size distribution under measurement.

INDUSTRIAL APPLICABILITY

As explained in the foregoing, the present invention is characterized by classifying particles suspended in a gas on the basis of their electric mobilities, then using the particle size measuring method to directly obtain estimated values of particle sizes, determining the number of charges of the particles from the estimated values of particle sizes thus obtained and the electric mobilities, and measuring the diameters of the particles with high precision from the number of charges thus determined and the electric mobilities. Since the particle size distribution therefore does not rely on the particle size measurement precision at the particle size measuring section if the flow volume Qa/Qc at the the electric mobility classifying section is set at a sufficiently small value, it is possible to measure the particle size distribution with high precision. Moreover, since this method does not require inverse problems to be solved, a particle size distribution can be obtained irrespective of the kind of particle size distribution under measurement.

What is claimed is:

1. A method for measuring particle size distribution, characterized by classifying particles suspended in a gas according to their electric mobilities, then using a particle size measuring method to directly obtain approximate values of particle sizes, obtaining the number of charges on the particles from the electric mobilities and the approximate particle sizes thus obtained, and determining the precise particle sizes from the number of charges thus obtained and the electric mobilities.

2. An apparatus for measuring particle size distribution, characterized by comprising an electric mobility classifying section (11) that comprises an outside electrode (12), an inside electrode (13) and an annular cylindrical hollow portion (14) defined by the outside and inside electrodes, a particle size measuring section (21) that is disposed under the electric mobility classifying section for measuring approximate particle sizes, and a guide frame (31) that allows the electric mobility classifying section and the annular cylindrical hollow section to communicate with each other; supplying from above a sample gas containing charged particles under measurement into the cylindrical hollow section of the electric mobility classifying section to classify the particles according to their electric mobilities; supplying the gas containing the classified particles into the particle size measuring section via the guide frame to directly obtain approximate particle sizes; obtaining the number of charges of the particles from the approximate particle sizes; and determining precise particle sizes from the number of charges and the electric mobilities.

* * * * *